United States Patent [19]

Snyder et al.

[11] 4,028,056

[45] June 7, 1977

[54] SUBSTANCE SEPARATION TECHNIQUE

[75] Inventors: Lloyd R. Snyder, Yorktown Heights; Bruce J. Oberhardt, Hartsdale; Jack Olich, Mahopac, all of N.Y.

[73] Assignee: Technicon Instruments Corporation, Tarrytown, N.Y.

[22] Filed: Apr. 20, 1976

[21] Appl. No.: 678,778

[52] U.S. Cl. .......................... 23/230 B; 23/230 R; 23/253 R; 23/292; 73/61.1 C; 210/24; 210/198 C; 210/DIG. 23

[51] Int. Cl.² .................. B01D 43/00; B01L 11/00; G01N 33/00; G01N 33/16

[58] Field of Search ......... 23/230 B, 253 R, 230 R, 23/292; 210/24 C, 198 C, DIG. 23; 73/61.1 C; 65/22 US

[56] References Cited

UNITED STATES PATENTS

| | | | |
|---|---|---|---|
| 3,241,432 | 3/1966 | Skeggs et al. | 23/253 R X |
| 3,549,524 | 12/1970 | Haller | 210/198 C X |
| 3,740,143 | 6/1973 | Groner et al. | 356/39 |
| 3,743,103 | 7/1973 | Isreeli et al. | 23/253 R X |
| 3,853,987 | 12/1974 | Dreyer | 23/230 B X |

Primary Examiner—Joseph Scovronek
Attorney, Agent, or Firm—S. P. Tedesco

[57] ABSTRACT

Apparatus and a method of separating a particulate portion as defined herein from a mixture including a liquid portion, including introducing the mixture into a stream of wash solution flowing along an open bore of a conduit, the wash solution having immiscible fluid segments therein, and subsequent to a separating step, collecting at least one of the aforesaid portions. Combined with these steps is the step of permeating over a period of time the internal surface of the aforementioned conduit with at least the aforementioned liquid portion. This retards the flow of the liquid portion which progressively lags behind the particulate portion until the two portions are separated by the segmented wash solution. Either or both portions may be collected, and when collected, the particulates are in washed condition. The aforementioned separation may be achieved on-line in a sample analyzer, and either or both collected portions may be reacted on-line with a reactant, and at least one product of the reaction may be analyzed on-line.

20 Claims, 8 Drawing Figures

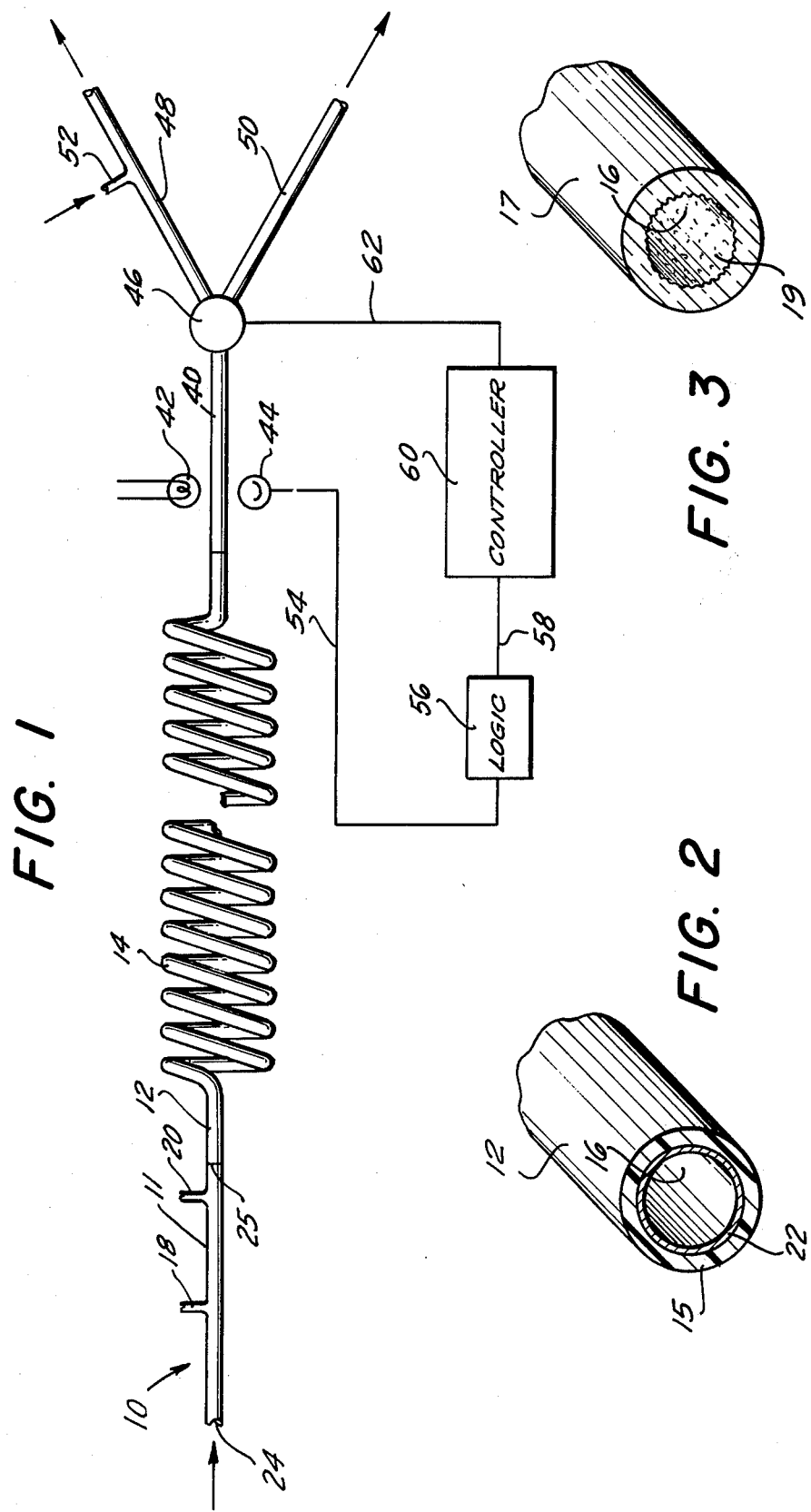

FIG. 4A FIG. 4B FIG. 4C FIG. 4D FIG. 5

SUBSTANCE SEPARATION TECHNIQUE

This invention relates to separating mixed substances according to their specific unit sizes, and relates more particularly to the separation from a mixture of units of a lesser specific unit size in a liquid from units of greater specific size which may take the form of particulates. For the purposes of this application, the term "particles" or "particulate matter" shall include solid particles and solutes dissolved or dispersed within a liquid such as blood protein with other liquid components.

Heretofore it has been common to separate substances of different specific densities by centrifugal force, and it is known that such centrifugal separation may take place on-line in a sample analyzer as in Negersmith et al U.S. Pat. No. 3,679,367. This involves relatively complex and expensive machinery. Further, it has been known to separate blood cells, for example, from the soluble constituents of a blood sample by these and other techniques including agglutination, clumping and settling. The last-mentioned techniques are time consuming and require the addition to the blood sample of a foreign substance which may interfere with analysis of such sample. Still another known type of separation process is that utilized in liquid chromatography or gel filtration, which has the disadvantage of not being utilizable to conduct therethrough a flow of liquid segmented with immiscible fluid segments as in continuous-flow analysis, and the further disadvantage of being unable to pass some types of particulates. Still another type of separation process involves separation of a constituent of a liquid by adherence or bonding to a coated internal wall of a test tube, which adherence is caused by absorption, including covalent bonding, or specific adsorption. The preparation of such a coated tube and such use is described in "Solid-Phase Radioimmunassay in Antibody-coated Tubes" by Kevin Catt and Geoffrey W. Tregear, *Science* 158: pp. 1570–1572 (1967). The coated tube in such separation processes is limited in its applications to use with particular substances for separation. The foregoing disadvantages of the prior art are overcome by the instant invention.

One object of the invention is to provide improved apparatus and method for separating a particulate portion from a mixture including a liquid portion. Another object is to provide such a separation in which the particulate portion is washed during separation. Further objects will be apparent from the following detailed description of the preferred embodiments of the invention.

In the drawings:

FIG. 1 is a fragmentary, broken, schematic top view illustrating apparatus embodying the invention;

FIG. 2 is a fragmentary view illustrating the construction of a tube portion of the apparatus;

FIG. 3 is a view similar to FIG. 2 illustrating a modified form of tube construction;

FIGS. 4A–4D are fragmentary, schematic, developed views of a portion of the apparatus of FIG. 1, illustrating the progressive separation of two components initially in a mixture when introduced into the apparatus, and showing respective sequential sections of such apparatus portion; and FIG. 5 is a fragmentary view similar to FIG. 4A illustrating a modified form of the invention.

In FIG. 1 of the drawings, a conduit is indicated generally at 10 comprising a tube 11 having an inlet 24 and an outlet 25 coupled to the inlet of a tube 12. By far the greater part of the length of the tube 12, if not its entire length, which may be six feet for example, is in the form of a coil 14. The tube 12 has an open bore 16 extending throughout the length thereof and the tube 11 is provided with longitudinally spaced T connections which provide inlets 18, 20. The construction of the tube 12 is best shown in FIG. 2 wherein there is illustrated an internal coating 22, which is applied throughout the internal surface area of the tube 12 which tube is open at both ends. The outer wall structure 15 of the tube 12 may be conveniently structured of a suitable plastic such as nylon resin and have an outer diameter of approximately 0.064 in. and internal diameter of approximately 0.034 in. The dimensions of the tube 12 may vary widely, depending somewhat on particular separations sought. Another material from which the tube 12 may be structured is polypropylene resin sold under the trademark Tygolene 800. The coating 22 may be of an inert porous substance which may be relatively very thin as on the order of 0.0015 in. or even less by way of example only. An appropriate technique for physically adhering such coating 22 to the tube 12 may be by etching such tube 12 formed of nylon with a 5.5 normal hydrochloric acid solution pumped through the tube 12 for 30 seconds. The tube 12 is rinsed immediately with water or saline, and subsequently a neutralizing solution of sodium hypochloride-sodium hydroxide is pumped through the tube 12. The tube 12 is then washed thoroughly with water or saline solution and thereafter dried. For adherence of the coating 22 to the inner wall of the tube 12, other techniques may be utilized to pit such surface, if necessary. For example, in preparing such a tube for adherence to such an internal coating 22, a tube constructed of Tygolene resin tubing may have the internal surface thereof pitted by the passage of fine steel wires or steel wool through the opening defined by the tube.

When the internal surface of the tube 12 has been prepared for adherence to the coating 22, the coating material, then in a molten state and which may be pumped through the tube 12, may comprise, for example, a 1.0 to 2.0% solution of argarose, which percentage determines the pore size of such coating in the finished product. The agarose penetrates the etched or pitted internal wall of the tube 12. When the molten agarose solution is pumped out of the tube, the coating 22 remains adhering to the internal surface of the tube wall. Other substances such as glass beads may be employed to provide the coating 22. It has been found that such a coating 22 may be omitted and the tube 12 utilized to perform the separation process of the invention in the pitted or etched condition previously described prior to the application of the coating 22 thereto. Such a tube 17 is shown in FIG. 3. It may be constructed of glass such as controlled pore glass, for example, the pitted internal surface thereof (achieved by an etchant or leaching agent) being indicated at 19. Hence, reference hereinafter to such a tube for a separation process may be construed as a tube having either an internal coating or no coating unless a contrary intention is expressly indicated.

Figures 4A, 4B, 4C, 4D, 5:
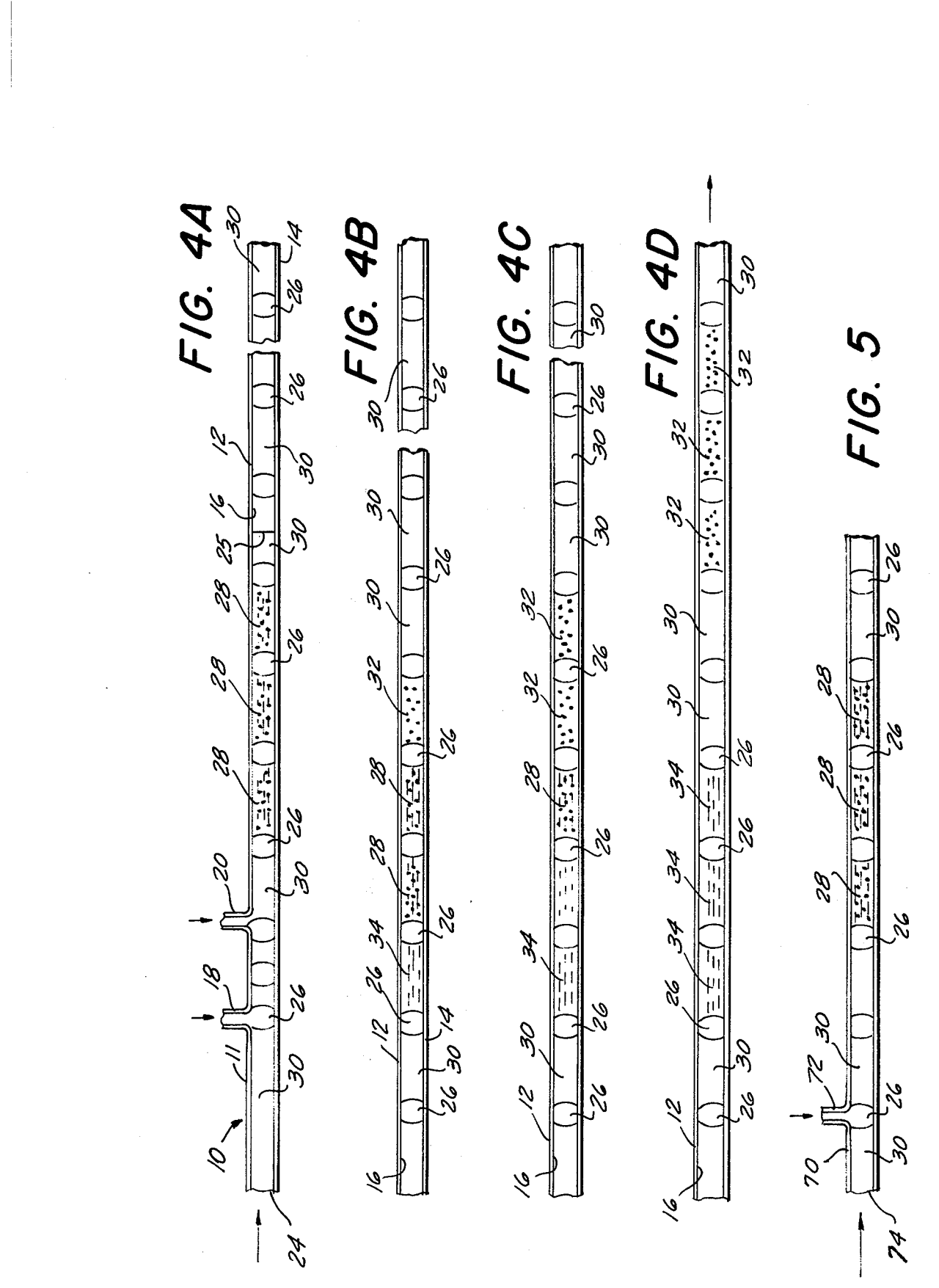

In the form of FIG. 1, a wash solution, which may be a saline solution or water, is introduced continuously in a conventional manner through the inlet end 24 for flow in the tubes 11, 12. A segmenting fluid is introduced in a conventional manner into the tube 11 through the inlet 18 at intervals to segment the wash solution in the tube 11 or, alternatively, not shown, the stream flowing into the inlet 24 may have such segments for flow through the tubes 11, 12 to the outlet end of tube 12. As shown in FIG. 4A, immediately following the intermittent introduction of the immiscible fluid segments 26, such segments are spaced from each other, as indicated, which spacing changes downstream of the inlet 20. The mixture to be separated, including a liquid and particulate matter, is introduced into the FIG. 11 immediately preceding a flow through the inlet 20 of a slug of wash solution and immediately following a slug of such wash liquid. Such mixture may be isolated from such slugs of wash solution during the introduction of the mixture by immiscible fluid segments in a resultant stream, as in Skeggs U.S. Pat. No. 3,241,432, and in which the segmenting fluid occludes the inlet 20 but not the tubes 11, 12. The above-described fluid introduction through the inlet 20 results in increased spacing of the immiscible fluid segments 26 in the tube 11, as shown in FIG 4A. The mixture is indicated at 28 and the wash solution at 30 in this view. As shown in the last-mentioned view the mixture 28 flowing in the tube 14 is segmented by the segments 26. The mixture 28 may be one of a series of discrete samples introduced through the inlet 20 sequentially, only one such mixture being shown in the drawings for the sake of clarity and simplicity. Depending somewhat on the nature of the substances which it is desired to separate, the immiscible fluid of the segments 26 may take the form of an inert gas or a suitable inert liquid. Further, such immiscible liquid segments may be employed in lieu of gas segments, particularly where the flow in the tube 12 may be subject to a tendency to surge, to avoid the compression of such segments formed of gas.

Following the above-described introduction through the inlet 20, the segmented stream flowing in the tube 12 enters the long mixing coil 14 thereof wherein, by reason of the immiscible fluid segments 26 in such stream, the contents of each liquid segment 28 containing particulates are thoroughly mixed in such a manner as to expose a large volume of the liquid portion of such segment 28 to the internal wall of the tube 12 which in this instance is provided with the coating 22. Such particulates are excluded or not excluded from the pores of the coating 22, while the liquid in these segments 28 enters the pores of such coating 22 more freely and then reenters the tube bore 16 in a repetitive manner to be retarded and progressively lag behind the particulate matter flowing along the tube 12 to produce the progressive separation of the particulate matter from the liquid of the mixture previously introduced into the tube 12 through the inlet 20. Of course, it is to be understood that the wash solution also freely enters and leaves the pores of the coating 22 to reenter the bore 16. As shown in FIG. 4B, the particulate matter becomes progressively mixed with, wash liquid, as in the segment 32, preceding in the flow the progressively separated liquid of the initial mixture 28 which liquid with wash solution becomes a liquid segment 34 in the flowing stream.

In such flow in the tube 12 over a period of time, the aforementioned immiscible fluid segments 26, if they consist of a gas, comprise a thin layer of liquid which interfaces with the coating 22 of the tube. Hence, each gas segment 26 moves along the coating 22 during the flow in a manner to pass any substance then permeating the coating portion in contact with such segment interface. If such immiscible segments consist of an immiscible liquid, which liquid should also be immiscible with the material of the coating 22 and the mixture, such immiscible liquid segments do not permeate the pores of the coating 22 due largely to the immiscibility of such liquid segments. Therefore, such immiscible liquid segments flow along the tube 14 interfacing with the coating 22 in a manner to pass any liquid and particles permeating the portions of the coating 22 which interface with the immiscible liquid segments.

In FIG. 4C, the particulate matter in purer form is shown downstream after a period of time mixed with the wash solution in segments 32 of the stream during the intermediate portion of the separation, with the more separated liquid of the aforementioned mixture being shown in segments 34. As the soluble liquid of the initial mixture continues to enter the porous coating of the tube and exit from such coating to reenter the bore 16 as the stream continues through the tube 12, the separation process continues and the liquid of that initial mixture lags farther and farther behind the segments of wash solution and particulate matter, until such segments containing the particulates contain a mixture of such particulates with the wash solution in a substantially purified form of the particulate matter upon complete separation of the initial mixture in the tube 12. The particles are washed in the separation process while the liqiud segments 34 of the stream which contain the liquid of the initial mixture, though still containing a proportion of a wash solution, are separated from the segments by segments of wash solution separated by immiscible fluid segments 26 as shown in FIG. 4D.

On completion of the separation of the liquid of the initial mixture from the particulate matter as shown in the last-mentioned view, the stream leaving the outlet end of the tube 12 flows through the tube 40 having an inlet end thereof coupled to the discharge end of the tube 12, which tube 40 is constructed of transparent glass. The tube 40 provides a "viewing area", at one side of which tube 40 is located a light source 42 and at the opposite side thereof is located a photo-detector 44. Light directed from the source 42 through the viewing area and impinging on the detector 44 indicates by a light loss when particulate matter is passing through the viewing area. In response to the presence in the viewing area of the particulate matter as indicated by the photodetector 44 and in phased relation to the fluid flow in tube 40, a three-way solenoid-operated valve 46, to which the outlet end of tube 40 is coupled to the inlet thereof, is operated to one position thereof to direct the liquid of the initial mixture through either outlet thereof and subsequently operated to the other position thereof to direct the particulate matter in wash solution through the other outlet thereof, as shown in FIG. 1. In the last-mentioned view, the liquid is directed through a tube 48 having an inlet thereof coupled to one outlet of the valve 46. The particulate matter in wash solution is directed to an inlet end of the tube 50 coupled to the other outlet of the valve 46. Either tube 48 or tube 50 may be considered an extension of the conduit 10.

As shown in FIG. 1, a signal from the photodetector 44 is directed along a lead 54 to a conventional logic circuit 56 which has an output through a lead 58 to a controller 60 which in turn has an output along lead 62 to the solenoid operated valve 46 to operate the latter for the sequencing of flow in the respective outlets of the valve 46 to the tubes 48 and 50.

A conventional treatment and examination (neither of which is illustrated) of the particulate matter (which may comprise white blood cells of the initial mixture which may be a whole blood sample) in conduit 50 may be accomplished utilizing the invention of Groner et al U.S. Pat. No. 3,740,143. In tube 48 a reactant such as a liquid reagent may be added through an inlet 52 to the liquid of the initial mixture, such as separated blood plasma of the aforementioned sample, and a reaction product, viewed in the conduit 48 in a conventional nonillustrated flowcell, may be analyzed for its optical density to indicate a concentration of a constituent of the plasma. If desired, the separated components from the mixture introduced into the inlet 18 may be collected in or from the tubes 48, 50. It should be noted that when the apparatus of FIG. 1 is not in use and the tube 12 is of the type having an internal coating of a gel such as agarose, the gel must be kept wet by maintaining a saline solution or water in the tube 12 in an appropriate manner.

In the modification shown in FIG. 5, the tube 11 of the form of FIG. 1 is replaced by a tube 70 which may be constructed of glass and which has single T connection forming an inlet 72 for a segmenting fluid. In a form of FIG. 5, the tube 70 has an inlet end 74 into which a slug of wash solution in the form of water or saline is introduced into the tube 70 immediately preceding the introduction through such inlet 74 of the mixture to be separated which mixture includes a particulate matter. On such introduction, the mixture is immediately followed by a slug of wash solution through the inlet 74. The flow in the tube 70 is similar to that described with reference to the apparatus of FIG. 1 with segments 26 therein of the segmenting fluid, which it will be noted do not undergo a change in spacing, flowing in the stream in the tube 70 wherein segments 28 of the mixture added thereto are the same as in the form of FIG. 1.

It will be readily apparent from the foregoing description that the invention may be utilized to separate more than two components from a mixture, and that the invention may be utilized to separate a soluble species such as blood protein from other, smaller unit size soluble components such as glucose or uric acid of a whole blood sample by allowing permeation into a porous internal surface of a tube such blood protein while permitting more freely permeation of such porous surface by other soluble components of the sample which are more retarded in flow.

EXAMPLE I

The apparatus of FIG. 5 was employed in an analysis for the quantitative determination of the constituent glucose in a sample of blood plasma. The reagent employed in this analysis for the detection of glucose was alkaline potassium ferricyanide.

Having specific reference to the apparatus of FIG. 5, 0.012 ml of a whole blood sample was introduced into the tube 70 at the inlet end 74 thereof immediately preceding and followed by slugs of wash solution in the form of 0.038 ml saline which stream was segmented by air introduced through the inlet 72. The tube 12 in this case has an outer wall structure of nylon and has an internal surface coated with 2.0% solution of agarose. The effective internal diameter of the tube 12 was 0.0393 in. and of a 7 ft. length in the form of a coil. The dwell time of the flowing sample in the tube 12 was 11.5 minutes. Both the saline wash solution and the sample were introduced into the inlet end 74 of the tube 70 at a rate of 0.10 ml per minute. Air introduced to segment the stream was introduced at a rate of 0.06 ml per minute. The sample which was introduced was one of a series of such samples and the rates of the introduction of each sample and the saline wash solution for flow through the tube 12 at the same rate were 7 seconds and 23 seconds, respectively. A gas segment was introduced every 2 seconds. The sample throughput was 120 samples per hour.

Each blood sample was separated in the tube 12 into the components of a cell portion and a plasma portion. The plasma portion was diverted by the valve 46 of FIG. 1 to the tube 48. The alkaline potassium ferricyanide reagent was added to the plasma portion of each sample in a volume ratio of 20:1 and the reagent and plasma portion were mixed in the tube 48 by a nonillustrated mixing coil interposed therein to achieve a colored reaction product which was analyzed quantitatively for glucose in a nonillustrated photometric manner in a flowcell, interposed in the tube 48, while passing through the tube 48 from which it was ultimately discharged. The valve 46 was also operated to divert the cell portion of each blood sample to the tube 50 from which the cells were discharged into a suitable collection vessel for conventional cytochemical studies.

EXAMPLE II

Blood cells of a whole blood sample were fixed by a fixative consisting of a 7.4% solution of formaldehyde in a sodium phosphate buffer having a pH of 6.7 and the excess fixative was separated from the fixed cells to render the latter free of contamination by such excess.

Having specific reference to the apparatus shown in FIG. 1 but in which the tube 12 was structured so as to have an exposed internal wall of etched nylon, the apparatus had a non-illustrated mixing coil interposed between the coil 14 and the tube 11, which interposed mixing coil was temperature controlled. Saline wash solution was flowed continuously into the inlet 24 of the tube 11. Through the inlet 18 were introduced intermittently immiscible segments of gas into the saline solution. A whole blood sample of 0.007 ml, one of a series for introduction through the inlet 20, was introduced through the last-mentioned inlet in combination with 0.006 ml of the fixative. The tube 12 was 4 ft. long and had an effective internal diameter of 0.0393 in. Preceding and following the introduction of each sample in the aforementioned combination with the fixative through the inlet 20, 0.037 ml of saline were introduced through the inlet 20. Each combined sample and fixative was mixed in the nonillustrated mixing coil interposed between the tubes 11 and 12 and the cell portion of each sample was fixed during incubation in the mixing coil. Thereafter, the cell portion of the sample was separated from the excess fixative in the tube 12 and the fixed cells were diverted to the tube 50 by the valve 46, and upon discharge from the tube 50 were collected for cytochemical studies. The sample throughput was 120 samples per hour.

EXAMPLE III

Antibodies were tagged with a fluorescent substance in a preparative procedure for analysis elsewhere of a sample utilizing these tagged antibodies. The excess fluorescent substance was separated from a mixture of the antibodies with such substance to remove any fluorescent substance not attached to the antibodies.

Having specific reference to the apparatus shown in FIG. 3 and in which the tube 17 was structured so as to have a non-porous outer wall structure but an internal porous surface 19 constructed by leading such tube according to the invention of Haller U.S. Pat. No. 3,549,524, the apparatus had a non-illustrated mixing coil interposed between the coil formed by the tube 17 and the tube 11 which interposed coil was not temperature controlled. Saline wash solution was flowed continuously into the inlet 24 of the tube 11. Through the inlet 18 were introduced intermittently immiscible segments of gas into the saline solution. The selected antibody in a saline solution in combination with the dye fluorescein isothiocyanate, one of a series of such combinations introduced intermittently through the inlet 20, was preceded and followed by slugs of saline solution. The reaction of the dye with the antibody occurred in the mixing coil interposed between tube 11 and the tube 17 during a four minute dwell time. Both the unbound dye and the antibody permeated the porous internal surface of the tube 17 with, the dye of lower molecule weight being more retarded in the flow through the tube 17 than the antibody so that separation was achieved between excess dye and the fluorescent antibody. The valve 46 of the apparatus of FIG. 1 was operated to flow the separated fluorescent antibody through the tube 50 for collection on discharge therefrom and for flowing the excess dye through the tube 48 for discharge therefrom to waste.

EXAMPLE IV

A quantity of commercial ink was separated into components suitable for spectrophotometric quantitation of the dyes in the ink. To make this analysis, the dyes were separated in a preparative procedure in the apparatus of FIG. 5 from a mixture including carbon black particulate matter. The dyes were soluble and the ink sample comprised a slurry of the aforementioned particulate matter and soluble matter.

Having specific reference to the apparatus of FIG. 5, 0.012 ml of the aforementioned mixture was introduced into the tube 70 at the inlet end 74 thereof immediately preceded and followed by slugs of wash solution in the form of 0.038 ml distilled water which stream was segmented by air introduced through the inlet 72 of the T connection of the tube 70. The tube 12 in this case had an outer wall structure of nylon and an internal surface coated with a 2.0% solution of agarose. The effective internal diameter of the tube was 0.0393 in. and the tube 12 was six feet in length and formed as a coil. The dwell time of the flowing sample in the tube 12 was approximately ten minutes. Each aforementioned wash solution slug and the aforementioned sample were introduced into the tube 70 as aforesaid at a rate of 0.10 ml per minute. Air introduced to segment the stream was provided at a rate of 0.06 ml per minute. The sample which was introduced was one of series of such samples taken from an ink production line. Sampling time was seven seconds and wash solution time was twenty-three seconds at the same flow rate. A gas segment was introduced every two seconds. The sample throughout was 120 samples per hour.

Each such sample was separated in the tube 12 into a dye phase which permeated the gel repeatedly in the tube 12 thereby being retarded in the flow of such dye phase. The aforementioned particulate matter, which did not permeate the gel, was not retarded in such flow through the tube 12. The dyes were diverted by the valve 46 of the apparatus FIG. 1 and collected in the tube 48 where they were analyzed spectrophotometrically while in flowing condition.

While several embodiments of the invention have been illustrated and described herein it will be readily apparent, especially to those versed in the art, that the invention may take other forms and is susceptible to various changes in details without departure from the principles of the invention.

What is claimed is:

1. A method of separating a particulate portion from a mixture including a liquid portion, comprising the steps of: introducing said mixture into a liquid stream flowing along an open bore conduit having an internal surface of porous configuration for permeation thereof by at least said liquid portion, segmenting said liquid stream with immiscible fluid segments during passage along said open bore of said conduit, permeating over a period of time the internal surface of said conduit with at least said liquid portion during the flow of said mixture along said open bore of said conduit to retard the flow of said liquid portion along said conduit and separating at least one of said portions.

2. A method as defined in claim 1, further including analyzing one of said separated portions during the flow thereof.

3. A method as defined in claim 1, further including permeating over a period of time the internal surface of said conduit with said particulate portion during said flow thereof to retard the flow of said particulate portion to a lesser extent than the flow of said liquid portion.

4. A method as defined in claim 1, further including permeating over a period of time the internal surface of said conduit with said liquid portion to the exclusion of said particulate portion.

5. A method as defined in claim 1, wherein: said mixture is a sample of whole blood and is separated in said flow in said conduit into a cell portion and a plasma portion.

6. A method as defined in claim 1, wherein: said particulate portion comprises blood cells and said liquid portion comprises an excess amount of fixative for said cells.

7. A method as defined in claim 1, wherein: said particulate portion comprises an antibody and said liquid portion comprises an excess amount of a dye for tagging said antibody.

8. A method as defined in claim 1, wherein: said mixture is introduced into said conduit in combination with another substance.

9. A method as defined in claim 1, further including mixing said mixture while flowing in said conduit.

10. A method as defined in claim 1, wherein: said mixture is an ink slurry, said particulate portion comprising carbon black and said liquid portion comprising dyes.

11. A method as defined in claim 1, wherein: said mixture is introduced into a portion of the liquid stream flowing in said conduit between immiscible fluid segments.

12. A method as defined in claim 1, wherein: said mixture is one of a series of samples introduced intermittently into said conduit.

13. A method as defined in claim 1, further including washing the particulates of said particulate portion in said liquid stream.

14. A method as defined in claim 3, wherein: said particulate portion comprises soluble blood protein and said liquid portion comprises other soluble components of smaller unit size.

15. Apparatus for separating a particulate portion from a mixture including a liquid portion, comprising: means flowing a liquid stream segmented with segments of an immiscible liquid along the length of an open bore conduit, said conduit length having an internal surface of porous configuration for permeation thereof by at least said liquid portion, said conduit having an outer wall structure of material impervious to the components of said mixture, and means introducing said mixture as a liquid segment into the stream in said conduit for flow of components thereof along said conduit.

16. Apparatus as defined in claim 15, wherein: said conduit is structured at least in part as a mixing coil.

17. Apparatus as defined in claim 15, further including means for analyzing one of said separated portions in an extension of said conduit during flow thereof in said extension.

18. Apparatus as defined in claim 15, further including valve and conduit means to divert one of said separated portions from said conduit for flow along said conduit means.

19. Apparatus as defined in claim 15, wherein: said mixture is a whole blood sample separated in said conduit portion into a cell portion and a plasma portion, said conduit being structured as a coil.

20. Apparatus as defined in claim 19, wherein: said conduit comprises an extension, and further including means introducing a reagent into said extension for reaction with one of said separated portions, and means analyzing a reaction product of the last-mentioned portion.

* * * * *